(12) United States Patent
Eviston

(10) Patent No.: US 12,714,004 B2
(45) **Date of Patent: *Aug. 25, 2026**

(54) METHOD AND DEVICE FOR DELIVERING BIOLOGICAL MATERIAL TO A MEDIUM

(71) Applicant: Meristem Crop Performance Group, LLC, Powell, OH (US)

(72) Inventor: Mitchell Eviston, Woodbury, MN (US)

(73) Assignee: Meristem Crop Performance Group, LLC, Powell, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/231,417

(22) Filed: Jun. 6, 2025

(65) Prior Publication Data

US 2025/0295053 A1 Sep. 25, 2025

Related U.S. Application Data

(63) Continuation of application No. 18/583,053, filed on Feb. 21, 2024, now Pat. No. 12,402,557, which is a (Continued)

(51) Int. Cl.
*A01C 1/06* (2006.01)
*A01C 1/08* (2006.01)
*C12N 1/20* (2006.01)

(52) U.S. Cl.
CPC .................. *A01C 1/06* (2013.01); *A01C 1/08* (2013.01); *C12N 1/20* (2013.01)

(58) Field of Classification Search
CPC .................................... A01C 1/06; A01C 1/08
See application file for complete search history.

(56) References Cited

U.S. PATENT DOCUMENTS 3,068,154 A * 12/1962 Majors .................. C12M 23/34 435/840
3,156,369 A * 11/1964 Bowes ................ B65D 51/285 215/250

(Continued)

FOREIGN PATENT DOCUMENTS

CN 207956518 U 10/2018
CN 113879693 A 1/2022

(Continued)

OTHER PUBLICATIONS

"Capods—Pre-Filled Unit Dose Caps," Lucas Packaging Group, Mar. 3, 2021, retrieved from https://lucaspackaging.com/capod/ [accessed on Apr. 16, 2025].

(Continued)

*Primary Examiner* — Monica L Perry
(74) *Attorney, Agent, or Firm* — Foley & Lardner LLP

(57) ABSTRACT

A device for delivering biological material includes a capsule including a cap portion to removably secure the capsule to a container and an elongate portion including a cavity with a frangible bottom, where the cavity includes biological material therein. The device further includes a plunger including walls defining an internal volume of the plunger, where the walls are moveable along an inner surface of the capsule when the plunger is depressed, and a shaft disposed within the internal volume and connected to a second end of the plunger, where the shaft includes a disrupting mechanism at a first end of the plunger for breaking the frangible bottom when the plunger is depressed. The first end of the plunger extends within the cavity of the capsule, and the second end of the plunger extends outward from the cavity and the elongate portion of the capsule.

20 Claims, 8 Drawing Sheets

Related U.S. Application Data continuation-in-part of application No. 18/503,899, filed on Nov. 7, 2023, now Pat. No. 12,402,556, which is a continuation of application No. 18/197,578, filed on May 15, 2023, now Pat. No. 11,812,685, which is a continuation of application No. PCT/US2023/012628, filed on Feb. 8, 2023.

(60) Provisional application No. 63/434,588, filed on Dec. 22, 2022.

(56) References Cited

U.S. PATENT DOCUMENTS 3,406,872 A * 10/1968 Fiquet .................... B65D 47/38 222/499
3,504,376 A 3/1970 Bednar et al.
3,715,189 A 2/1973 Nighohossian et al.
3,968,872 A * 7/1976 Cavazza .............. B65D 51/285 604/416
4,103,772 A 8/1978 Wiegner
4,195,730 A 4/1980 Hunt
4,283,498 A * 8/1981 Schlesinger ....... A61B 10/0051 600/584
4,306,357 A * 12/1981 Villarejos ............ B65D 51/241 34/284
4,640,895 A 2/1987 Davis
4,785,931 A 11/1988 Weir et al.
4,903,865 A * 2/1990 Janowitz ............ B65D 51/2842 604/416
5,431,276 A 7/1995 Lialin
5,507,133 A * 4/1996 Singleton ............... C12M 45/22 53/239
5,772,017 A * 6/1998 Kang ................. B65D 51/2842 426/115
5,979,647 A 11/1999 Han
6,148,996 A 11/2000 Morini
6,959,839 B2 * 11/2005 Roth .................... B65D 47/243 222/145.5
6,976,578 B1 12/2005 Kenihan
7,607,549 B2 * 10/2009 Morini ............... B65D 41/3438 220/259.2
8,297,456 B1 10/2012 Anderson
8,308,075 B2 * 11/2012 Eastin ....................... D01F 9/00 239/1
8,443,970 B2 5/2013 Coon
8,453,834 B2 6/2013 Porter
8,584,840 B2 11/2013 Kim
8,770,399 B2 7/2014 Hjalmarsson
9,174,881 B2 11/2015 Cimaglio et al.
9,260,740 B2 2/2016 Sharpin
10,065,775 B2 * 9/2018 Estes .................. B65D 41/3428
10,285,908 B2 5/2019 Mittal et al.
10,369,078 B2 * 8/2019 Bhargava .............. A61J 1/2093
10,774,298 B2 * 9/2020 Caldwell ................ A01N 63/22
12,060,199 B2 8/2024 Den Boer et al.
12,091,222 B2 9/2024 Den Boer et al.
12,116,173 B2 10/2024 Den Boer et al.
12,402,557 B2 9/2025 Eviston
12,546,101 B2 2/2026 Rice et al.
2006/0154363 A1 * 7/2006 Horn ...................... C12M 23/14 435/304.2
2006/0236925 A1 * 10/2006 Lund ........................ A01C 1/06 118/19
2008/0142473 A1 * 6/2008 Cho ..................... B65D 51/285 215/329
2008/0293156 A1 11/2008 Smith
2008/0314775 A1 * 12/2008 Owoc ................ B65D 55/0854 206/222
2009/0048128 A1 2/2009 Custis et al.
2010/0044377 A1 2/2010 Porter
2011/0049081 A1 3/2011 Bourguignon
2012/0061421 A1 * 3/2012 Roth .................... B65D 47/243 222/521
2013/0139703 A1 6/2013 Hogarth
2015/0360844 A1 12/2015 Frieden
2016/0053218 A1 * 2/2016 Caldwell ................ A01N 63/20 435/256.7
2018/0148220 A1 5/2018 Kincaid
2018/0177192 A1 * 6/2018 Johnson ................. A01N 25/08
2020/0347336 A1 * 11/2020 Caldwell ................ A01N 63/20
2021/0171254 A1 6/2021 Love et al.
2024/0206368 A1 6/2024 Eviston

FOREIGN PATENT DOCUMENTS

CN 215476947 U 1/2022
JP 3002282 U 9/1994
KR 101818944 B1 2/2018
WO WO-2018/098254 A1 5/2018
WO WO-2018/109018 A1 6/2018

OTHER PUBLICATIONS

"Fresh Beverages International—Shinsen Cap," No Time Like the Present, Apr. 7, 2017, retrieved from https://ntltp.com/fresh-beverages-international/ [accessed on Apr. 16, 2025].
Bouckley, Ben, "'Unique' bottle dosing and dispensing cap boosts brand visibility: Tap the Cap," Beverage Daily, Oct. 23, 2012, retrieved from https://www.beveragedaily.com/Article/2012/10/24/Unique-bottle-dosing-and-dispensing-cap-boosts-brand-visibility-Tap-the-Cap/ [accessed on Apr. 16, 2025].
Steeman, Anton, "Innovative Dispensing Bottle Caps for Sensitive Vitamins," Best in Packaging, May 29, 2009, retrieved from https://bestinpackaging.wordpress.com/2009/05/29/innovative-dispensing-bottle-caps-for-sensitive-vitamins/ [accessed on Apr. 16, 2025].
International Preliminary Report on Patentability Transmittal on PCT PCT/US2023/012628 Dtd Jul. 3, 2025.
International Search Report on PCT PCT/US2023/012628 Dtd Sep. 14, 2023.
International Search Report on PCT PCT/US2025/016460 Dtd Jun. 2, 2025.
MX Office Action on MX/a/2025/007427 Dtd Jun. 24, 2025.

* cited by examiner

METHOD AND DEVICE FOR DELIVERING BIOLOGICAL MATERIAL TO A MEDIUM

CROSS-REFERENCE TO RELATED PATENT APPLICATIONS

This application is a Continuation of U.S. patent application Ser. No. 18/583,053 filed on Feb. 21, 2024, which is a Continuation-In-Part of U.S. patent application Ser. No. 18/503,899 filed on Nov. 7, 2023, which claims priority and benefit of U.S. Provisional Patent Application No.: 63/434,588, filed Dec. 22, 2022, which is a Continuation of U.S. application Ser. No. 18/197578 filed on May 15, 2023, which claims priority and benefit from U.S. Provisional Patent Application No.: 63/434,588, filed Dec. 22, 2022, and which is a Continuation of International Application No. PCT/US2023/012628, filed Feb. 8, 2023, which claims priority and benefit of from U.S. Provisional Application Patent Application No.: 63/434,588 filed on Dec. 22, 2022, the contents of each which are incorporated herein by reference in their entireties.

BACKGROUND

The present disclosure relates to the storing and delivery of contents to a liquid medium and more specifically to a capsule for the storage and delivery of biological material to a liquid medium for application to plants and/or soil.

Farmers use soil and foliar applications for a variety of reasons including to fertilize crops, control pests and diseases, and promote crop residue breakdown. Foliar application is applying agricultural inputs (e.g., fertilizers, insecticides) directly to the leaves of a plant, not just the soil, where they can be absorbed through the leaf surface and utilized by the plant. Many applications utilize biological material (e.g., microorganisms) along with an agricultural input to promote necessary plant processes (e.g., fertilization, pest control). However, many species of microorganisms are fragile and cannot survive long-term outside of their natural environment, thus they cannot be premixed without reducing efficacy of the agricultural input.

SUMMARY

An aspect of the present disclosure relates to a device for delivering biological material to a liquid medium including a capsule and a plunger. The capsule includes a cap portion configured to removably secure the capsule to a mouth of a container and an elongate portion including a cavity defined at least in part by a frangible bottom, where the cavity includes biological material therein. The plunger includes a first end and a second end, one or more walls defining an internal volume of the plunger, where the one or more walls moveable along an inner surface of the capsule when the plunger is depressed, and a shaft disposed at least partially within the internal volume and connected to the second end of the plunger, where the shaft includes a disrupting mechanism at the first end of the plunger and the disrupting mechanism is positioned external to the internal volume of the plunger, where the disrupting mechanism is configured to break the frangible bottom when the plunger is depressed. The first end of the plunger extends within the cavity of the capsule, and the second end of the plunger extends outward from the cavity and the elongate portion of the capsule.

In some embodiments, the one or more walls defining the internal volume of the plunger are moveable in an axial direction relative to the capsule when the plunger is depressed. In some embodiments, the biological material is retained within the internal volume of the plunger between the one or more walls and the frangible bottom of the capsule, where the biological material is forced out of the cavity of the capsule by the plunger when the plunger is depressed. In some embodiments, the plunger further includes a shoulder portion configured to retain at least the first end of the plunger within the cavity of the capsule when the plunger is in a non-depressed state. In some embodiments, the elongate portion of the capsule includes a shoulder portion configured to interfere with the shoulder portion of the plunger to retain the plunger at least partially within the capsule. In some embodiments, the device further includes a sealing member disposed between the one or more walls of the plunger and the inner surface of the capsule.

In some embodiments, the device further includes a locking mechanism configured to prevent the plunger from being depressed. The locking mechanism is slidable on the plunger. In some embodiments, the device further includes a plunger cap connected to the second end of the plunger, where the locking mechanism engages the plunger, and the plunger cap maintains the locking mechanism in position between the plunger cap and the elongate portion of the capsule until manual removal of the locking mechanism by a user. In some embodiments, the locking mechanism includes a ring portion and a tearable portion, where the locking mechanism is configured for manual removal by a user by separating the tearable portion from the ring portion and pulling the ring portion off of the plunger.

Another aspect relates to a system for delivering biological material to a liquid medium. The system includes a container including the liquid medium. The system further includes a capsule and a plunger. The capsule includes a cap portion configured to removably secure the capsule to a mouth of the container and an elongate portion including a cavity defined at least in part by a frangible bottom, where the cavity includes biological material therein. The plunger includes a first end and a second end, one or more walls defining an internal volume of the plunger, where the one or more walls moveable along an inner surface of the capsule when the plunger is depressed, and a shaft disposed at least partially within the internal volume and connected to the second end of the plunger, where the shaft includes a disrupting mechanism at the first end of the plunger and the disrupting mechanism is positioned external to the internal volume of the plunger, where the disrupting mechanism is configured to break the frangible bottom when the plunger is depressed. The first end of the plunger extends within the cavity of the capsule, and the second end of the plunger extends outward from the cavity and the elongate portion of the capsule.

In some embodiments, the container is a plastic F-style container. In some embodiments, a volume of the container is approximately 2.5 gallons.

In some embodiments, the one or more walls defining the internal volume of the plunger are moveable in an axial direction relative to the capsule when the plunger is depressed. The biological material is retained within the internal volume of the plunger between the one or more walls and the frangible bottom of the capsule, where the biological material is forced out of the cavity of the capsule by the plunger when the plunger is depressed. The plunger further includes a shoulder portion configured to retain at least the first end of the plunger within the cavity of the capsule when the plunger is in a non-depressed state.

In some embodiments, the system further includes a locking mechanism configured to prevent the plunger from being depressed, where the locking mechanism includes a ring portion and a tearable portion. The system further includes a plunger cap connected to the second end of the plunger, where the locking mechanism engages the plunger, and the plunger cap maintains the locking mechanism in position between the plunger cap and the elongate portion of the capsule until manual removal of the locking mechanism by a user separating the tearable portion from the ring portion and pulling the ring portion off of the plunger.

Another aspect relates to a method for delivering biological material to a liquid medium. The method includes securing a capsule to a mouth of a container, where the capsule includes a cap portion configured to removably secure the capsule to a mouth of the container and an elongate portion includes a cavity defined at least in part by a frangible bottom, where the cavity includes biological material therein. The method further includes suspending the elongate portion of the capsule into a cavity of the container. The method further includes depressing a plunger, where the plunger includes a first end and a second end; one or more walls defining an internal volume of the plunger, where the one or more walls moveable along an inner surface of the capsule; and a shaft disposed at least partially within the internal volume and connected to the second end of the plunger, where the shaft includes a disrupting mechanism at the first end of the plunger and the disrupting mechanism is positioned external to the internal volume of the plunger. The first end of the plunger extends within the cavity of the capsule, and the second end of the plunger extends outward from the cavity and the elongate portion of the capsule. The method further includes disrupting the frangible bottom of the capsule and releasing the biological material into the container.

In some embodiments, the method further includes removing a locking mechanism from the plunger to allow depression of the plunger, where the locking mechanism is engaged with the plunger in position between the elongate portion of the capsule and a plunger cap connected to the second end of the plunger. In some embodiments, removing the locking mechanism includes separating a tearable portion from a ring portion of the locking mechanism, and pulling the ring portion of the locking mechanism off of the plunger.

In some embodiments, releasing the biological material into the container includes forcing the biological material into the container using the plunger. In some embodiments, the method further includes shaking the container to combine the biological material with a liquid medium provided within the container. In some embodiments, the biological material includes a bio-fungicide, bio-herbicide, bio-fertilizer, and/or bio-insecticide/pesticide.

BRIEF DESCRIPTION OF THE DRAWINGS

FIG. 1A is a perspective view of a capsule for delivery of biological material according to one or more embodiments herein.

FIG. 1B is a perspective view of a capsule in an activated state according to the embodiment in FIG. 1A.

DETAILED DESCRIPTION

Figure 2:
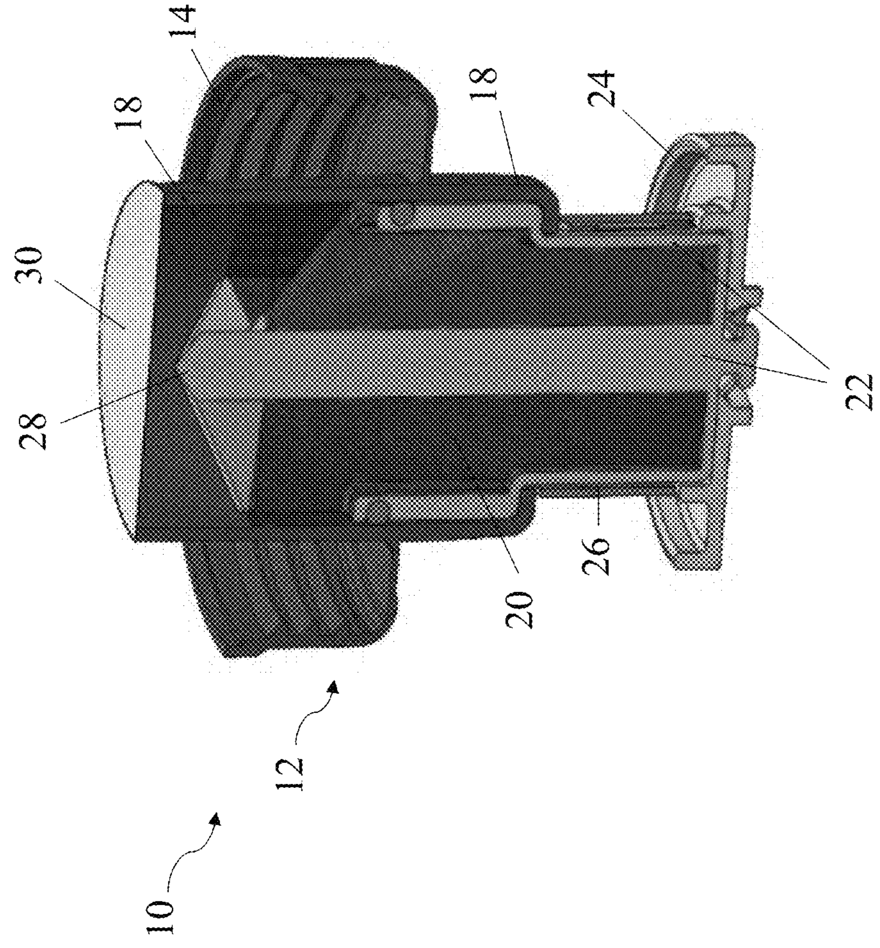
FIG. 2 is a cross-section view of a capsule for delivery of biological material according to one or more embodiments herein.

Described herein is a device for delivery of biological material to a liquid medium. The device provides a sealed, closed environment that keeps the biological material live and/or viable and disperses the biological material into a medium to be applied to plants and/or soil. The medium may be a liquid medium for spray applications such as foliar and/or soil applications.

The biological material may be chemical and/or biological material. The chemical and/or biological material may be one or more chemical agents, biological agents, organisms, microorganisms, cells, viruses, proteins, compounds, molecules, etc. The chemical agents or biological agents may include fungicides, insecticides, nematicides, plant growth regulators, fertilizers, micronutrients, etc. The chemical agents are generally synthetic whereas the biological agents are generally natural (e.g., bio-fungicides, etc.). Microorganisms may include bacteria, fungi, etc. Proteins may include enzymes, structural proteins, transport proteins, hormones, antibodies, receptor proteins, etc. The biological material includes live and/or viable biological material. For example, the live and/or viable biological material may be active, functioning, exhibiting biological processes such as growth and metabolism, capable of surviving and reproducing in its environment, etc.

The liquid medium may be one or more of water, fungicides, insecticides, nematicides, plant growth regulators, fertilizers, micronutrients, compounds, molecules, etc. In one or more embodiments, the liquid medium may be a foliar and/or soil nutrient product, fungicide, insecticide, and/or herbicide. The liquid medium may be and/or comprise Excavator and/or Microbilize.

Fungicides (bio-fungicides) can include: *Trichoderma* spp., *Bacillus* spp., *Pseudomonas* spp., *Streptomyces* spp., *Gliocladium* spp., *Bacillus thuringiensis* (Bt), *Coniothyrium minitans, Ulocladium oudemansii, Clonostachys rosea*, and other biological species labeled and registered as, or for, fungicidal activity.

Insecticides/pesticides (bio-insecticides/pesticides) can include: *Bacillus thuringiensis* (Bt), *Beauveria bassiana,*

*Metarhizium anisopliae, Heterorhabditis bacteriophora, Steinernema feltiae*, spinosad-producing bacteria, *Paecilomyces fumosoroseus*, entomopathogenic viruses, chitinolytic bacteria and fungi, *Pseudomonas fluorescens, Trichoderma* spp., azadirachtin-producing microbes, *Methylorubrum extorquens*, and other biological species labeled and registered as, or for, insecticidal activity. For example, *Methylorubrum extorquens* strain NLS0042.

Herbicides (bio-herbicides) can include: *Phoma macrostoma, Colletotrichum gloeosporioides* f. sp. *aeschynomene, Fusarium oxysporum* f. sp. *strigae, Phytophthora palmivora, Alternaria alternate, Xanthomonas campestris* pv. *poae, Pyricularia oryzae, Rhopalosiphum padi* virus (RhPV), and other biological species labeled and registered as, or for, herbicidal activity.

Fertilizers (bio-fertilizers) can include: *Rhizobium* spp., *Azotobacter* spp., *Azospirillum* spp., phosphate-solubilizing bacteria (PSB), mycorrhizal fungi, cyanobacteria, and *Acetobacter diazotrophicus, Actinomycetes, Bacillus amyloliquefaciens*, and other biological species labeled and registered as, or for, effecting overall plant fertility activity. For example, *Bacillus amyloliquefaciens* strain ENV503.

The chemical and/or biological material or the medium may include one or more of Glyphosate, 2,4-Dichlorophenoxyacetic acid (2,4-D), Dicamba, Atrazine, Paraquat, Azoxystrobin, Boscalid, Mancozeb, Myclobutanil, Thiophanate-methyl, Chlorpyrifos, Imidacloprid, Malathion, Permethrin, Deltamethrin, and other biological chemical and biological material labeled and registered as, or for, pesticidal activity.

In one or more embodiments, the biological material may be from the soil, plants, or other naturally occurring biological environments. In other words, a natural environment for the biological material may be the soil, plants, and/or water. In one or more embodiments, the device is configured to mimic a natural environment of the biological material so the biological material can be stored for longer periods of time. If the biological material is added to a medium, such as a liquid medium, the biological material may only survive for a short period of time. Additionally, or alternatively, the device may keep the biological material separate from the medium. The device provides efficient and effective storage and delivery of live and/or viable biological material.

Furthermore in one or more embodiments, synthetic chemistries may also be included such as conventional herbicides, fungicides, pesticide, insecticides or fertilizers.

The device described herein may be a capsule that is securable to a mouth or opening of a container for dispersing biological material into the container. Live biological material includes live and/or viable biological material. The capsule may be configured to store and maintain biological material long-term and until a time for use. The capsule may contain up to about 50 mL, 125 mL, 350 mL, 500 mL, 1 L, or more of biological material therein. The capsule may be selectively deployed by a user into a container containing a medium, such as a liquid medium. The liquid medium containing the biological material may then be applied to plants and/or the earth. The biological material may be applied to plants and/or soil for various purposes. For example, they can contribute to pest and disease control, nitrogen fixation, plant growth, weed control, bioremediation, crop residue breakdown, etc.

The device comprises a capsule body having a cap portion for securing to a mouth or opening of a container and an elongate portion for storing chemical and/or biological material before deployment. In one or more embodiments, the cap portion may comprise one or more threads such that the cap portion is threadably securable to the mouth of the container. Other methods of securing the capsule body are also contemplated. The elongate portion is configured to receive a plunger therein such that the plunger may be activated by a user to disperse the chemical and/or biological material into a reservoir of the container. In one or more embodiments, the elongate portion comprises a frangible bottom such that the plunger may disrupt the frangible bottom to disperse the chemical and/or biological material into the container. The chemical and/or biological material may be stored within the elongate portion and/or the plunger.

The elongate portion may be a tube or channel comprising a cavity for storage of chemical and/or biological material. The cavity may be defined by wall(s) and a frangible bottom of the elongate portion. The elongate portion may be suspended within, or above, a container when the capsule body is secured to the mouth of the container. A first end of the elongate portion located within the container may have the frangible bottom. The frangible bottom may separate contents within the capsule from contents within the container. The frangible bottom may be ruptured or broken to add the contents of the capsule to the contents of the container in the reservoir of the container. The frangible bottom may be a frangible membrane, foil, or any other material that may be disrupted by the plunger.

The size and dimensions of the capsule body may vary, allowing the device to be used on any commercially available or custom designed container. The cap portion of the capsule body may be configured to screw/thread on the mouth of a container in the same manner as a factory cap of the container. For example, the cap portion may be a standard size and/or 63 mm. The elongate portion may have a diameter smaller than a diameter of the mouth of a container. A length of the elongate portion may also vary depending on the application and/or container size/volume. For example, a length of the elongate portion may be about 1-12 inches for a 1-gallon or 2.5 gallon container. A capsule volume may be proportional to a container volume. In one or more embodiments, a capsule volume is less than 25% of a container volume. For example, the capsule volume may be 10% of the container volume. In one or more embodiments, a length of the elongate portion is configured to be in contact with contents of the container such that capsule body contents are dispersed directly into the contents of the container. In an alternative embodiment, a length of the elongate portion is configured such that the capsule body is adjacent the contents of the container.

The size and dimensions of a container may vary, allowing the device to be used for a variety of applications and operations. A size/volume of a container may be 2.5 gallons, 1 gallon, 1 pint, 1 quart, etc. The container may be a 125-gallon or 250-gallon tote. In one or more embodiments, a container is a jug or F-Style container. For example, the container may be a plastic 2.5-gallon F-Style container. A distinctive feature of an F-style container is its narrow mouth or opening, which is usually accompanied by a screw cap. The size and dimensions of the capsule maybe scaled up or down to accommodate larger or smaller containers. In addition, the cap portion diameter may be increased or decreased to accommodate an opening of any container.

The plunger may be configured to be receivable within the elongate portion of the capsule body and may be activated to release the contents stored therein. The plunger may be one or more deployment mechanisms configured to rupture a floor or wall which acts as a dividing member separating the contents of the device from the reservoir chamber of the container. The plunger may comprise a cutting or disrupting mechanism for disrupting a frangible bottom on the capsule body allowing chemical and/or biological material to be released into the container. The disruption may be from a blunt or a sharp element in the capsule body and/or on the plunger being displaced to displace or puncture the wall or floor of the capsule body and/or may comprise a change in the pressurization of the capsule body thus rupturing or displacing the wall(s) and/or floor of the capsule body. Other mechanisms include a plunger mechanism, puncture mechanism, slice mechanism, tearing mechanism, pealing mechanism, air pressure mechanism to effectively pop the capsule body or combinations thereof.

In one or more embodiments, the device further comprises a locking mechanism to prevent premature activation of the plunger and/or deploying of chemical and/or biological material. The locking mechanism may be a ring configured to engage a portion of the plunger opposing a cutting or disrupting mechanism. Additionally, or alternatively, the locking mechanism may be located near a portion of the plunger that a user engages to activate the plunger and/or deploy capsule contents. The locking mechanism may be removed before the plunger may be activated. In one or more embodiments, removal of the locking mechanism exposes the plunger for activation by a user.

In one or more embodiments, the device further comprises a plunger cap. A plunger cap may be configured for use on a portion of the plunger opposing a cutting mechanism and/or near a portion of the plunger that a user engages to activate the plunger. The plunger cap may keep a locking mechanism in place until the locking mechanism is removed by a user. Thus, the plunger cap may assist in preventing premature and/or accidental deployment of capsule contents. Additionally, or alternatively, the plunger cap may provide an easier target for a user to activate the plunger. For example, the plunger cap may have a greater diameter or area for a user to engage. The plunger cap may assist a user in selectively dispersing chemical and/or biological material into a container.

Also described herein is a method of delivering chemical and/or biological material to a liquid medium. In one or more embodiments, a capsule is secured to a mouth or opening of a container. The capsule may comprise a cap portion for threadably securing to the mouth of the container and an elongate portion extending into an interior cavity of the container when the capsule is secured. The capsule may further comprise a cavity defined by the elongate portion and a frangible bottom for hosting chemical and/or biological material therein. The frangible bottom may separate the chemical and/or biological material from contents of the container.

The method further comprises activating a plunger to disperse the chemical and/or biological material. In one or more embodiments, activating the plunger disrupts the frangible bottom of the capsule thereby releasing the contents therein. For example, the plunger may be activated by depressing the plunger and/or pushing the plunger toward the frangible bottom. The plunger may disrupt the frangible bottom by puncturing, popping, breaking, tearing, etc.

In one or more embodiments, the method further comprises removing a locking mechanism. For example, the locking mechanism may be a ring configured to engage the plunger and prevent premature release of capsule contents.

In one or more embodiments, the method further comprises engaging a plunger cap to activate the plunger. For example, the plunger cap may be engaged by depressing the plunger cap and/or pushing the plunger cap toward the plunger.

In one or more embodiments, the method further comprises removing a factory cap. A container may be provided with a factory cap and the factory cap may be removed before securing the capsule to a mouth of a container.

In one or more embodiments, the method further comprises shaking the container to combine the contents and/or removal of the capsule after use of the capsule. The capsule may be removed, and the factory cap may be replaced until it's time to use the mixture. At a time for use, the mixture may be applied directly to a plant and/or soil or the mixture may be combined with other products before use.

Figures 1A, 1B:
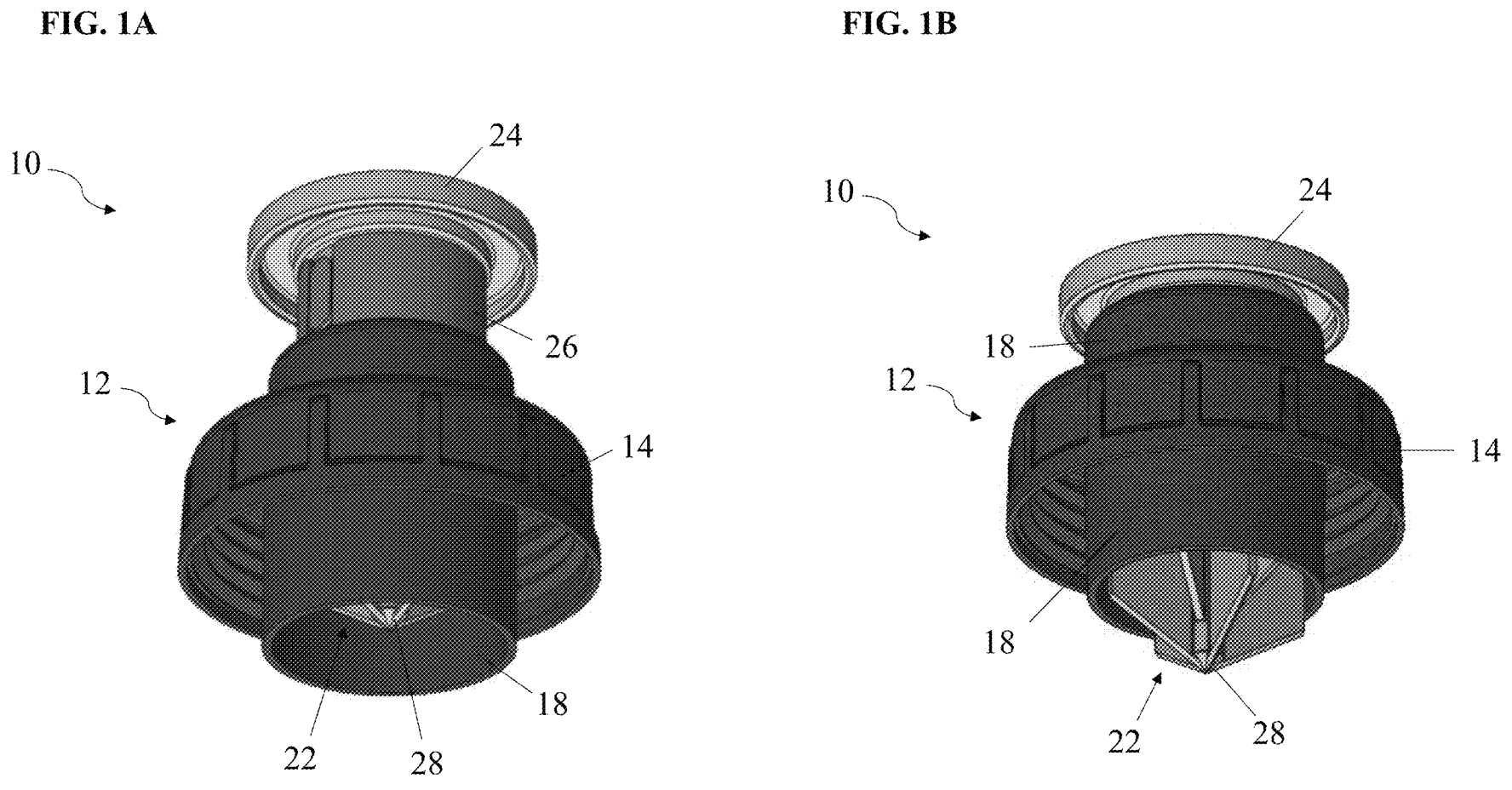

A capsule 10 is illustrated in FIGS. 1-4. The device 10 comprises a capsule body 12 having a cap portion 14 for threadably securing to a mouth or opening of a container 16 and an elongate portion 18 for storing chemical and/or biological material 20 before deployment. The elongate portion 18 is configured to receive a plunger 22 therein such that the plunger 22 may be activated by a user to disperse the chemical and/or biological material 20 from the capsule body 12 into a reservoir of the container 16. The elongate portion 18 and the plunger 22 collectively store chemical and/or biological material 20 therein.

Figures 4A, 4B:
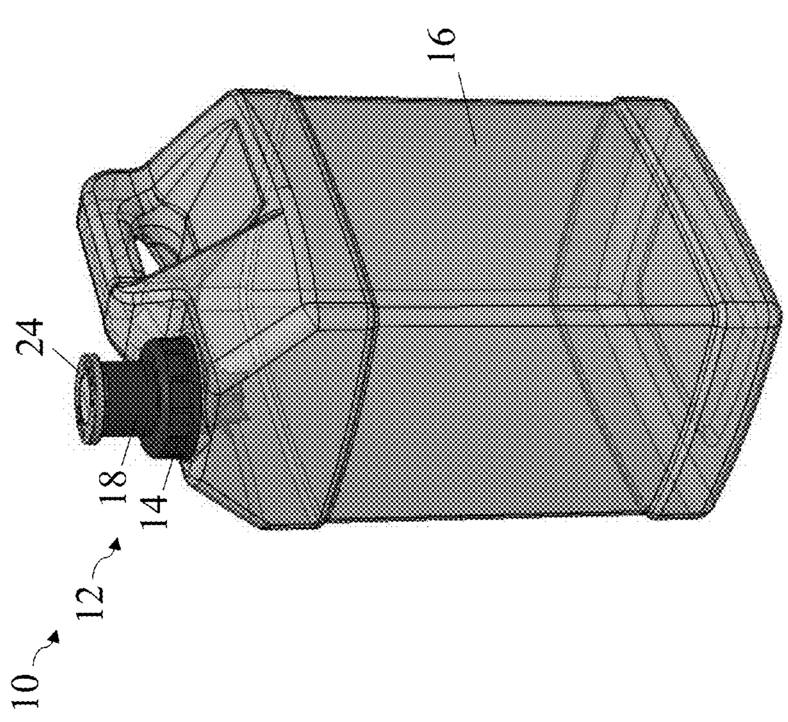
FIG. 4A is a perspective view of a capsule in an activated state and installed on a container according to one or more embodiments herein.
FIG. 4B is a perspective view of a capsule in an activated state and installed on a container according to the embodiment in FIG. 4A.
Figures 5A, 5B:
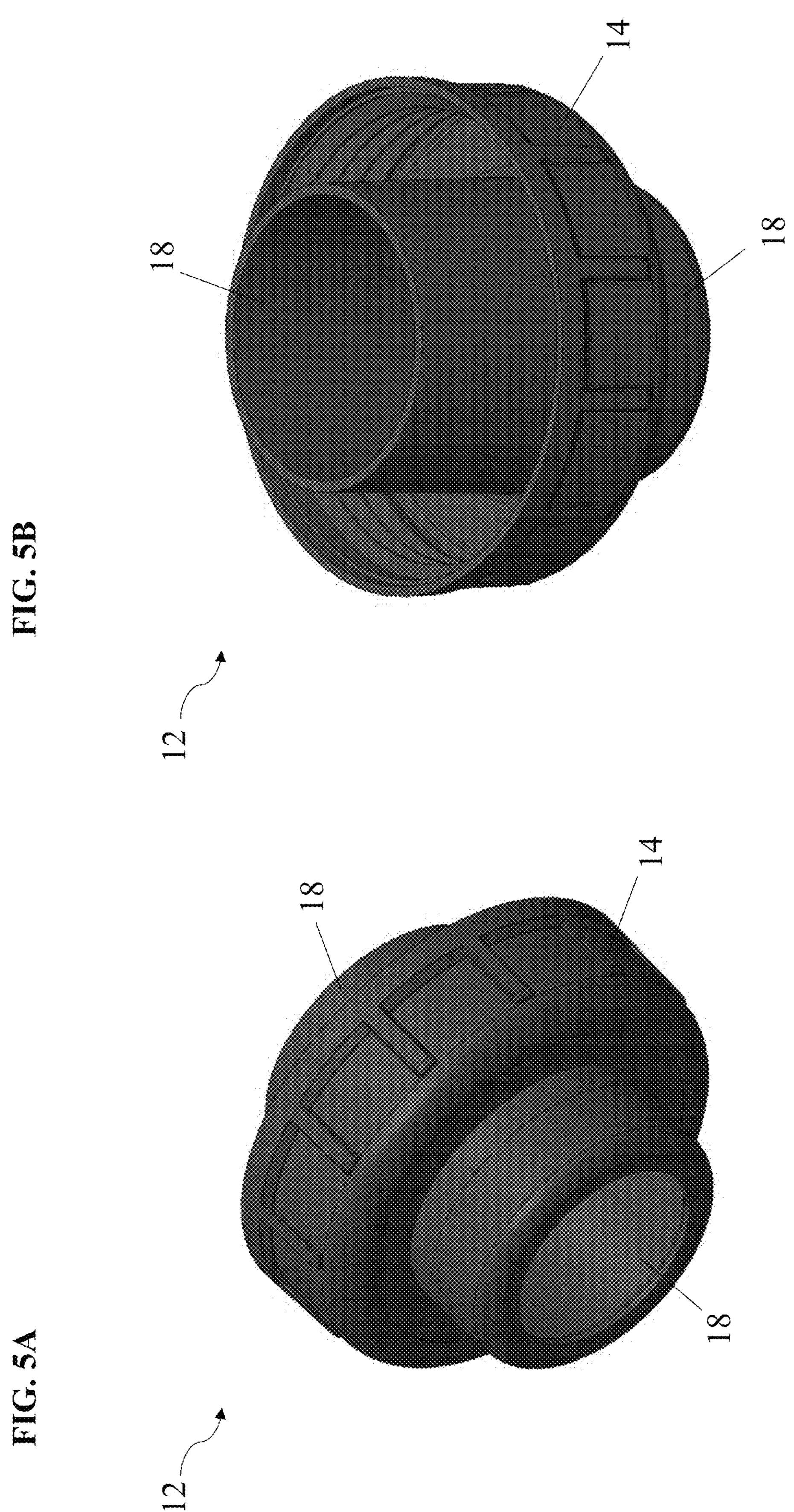
FIG. 5A is a perspective view of a capsule body according to one or more embodiments herein.
FIG. 5B is a perspective view of a capsule body according to the embodiment in FIG. 5A.
Figure 6B:
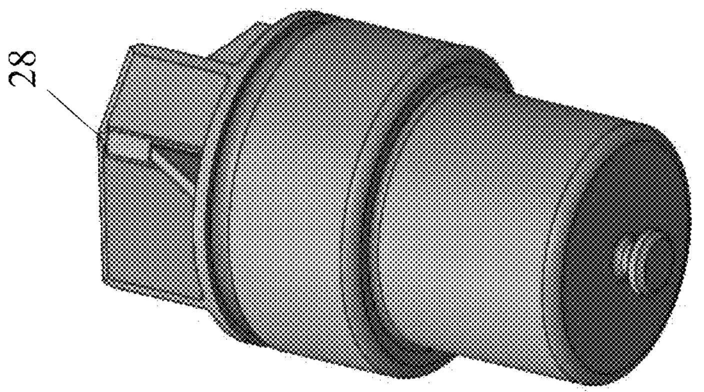
FIG. 6B is a perspective view of a plunger according to the embodiment in FIG. 6A.
Figure 6B:
Figure 6A:
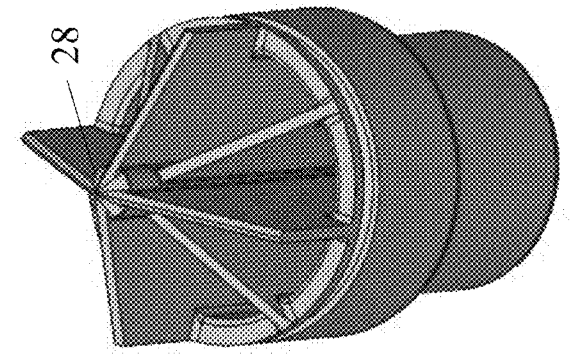
FIG. 6A is a perspective view of a plunger according to one or more embodiments herein.
Figure 6A:
Figure 7B:
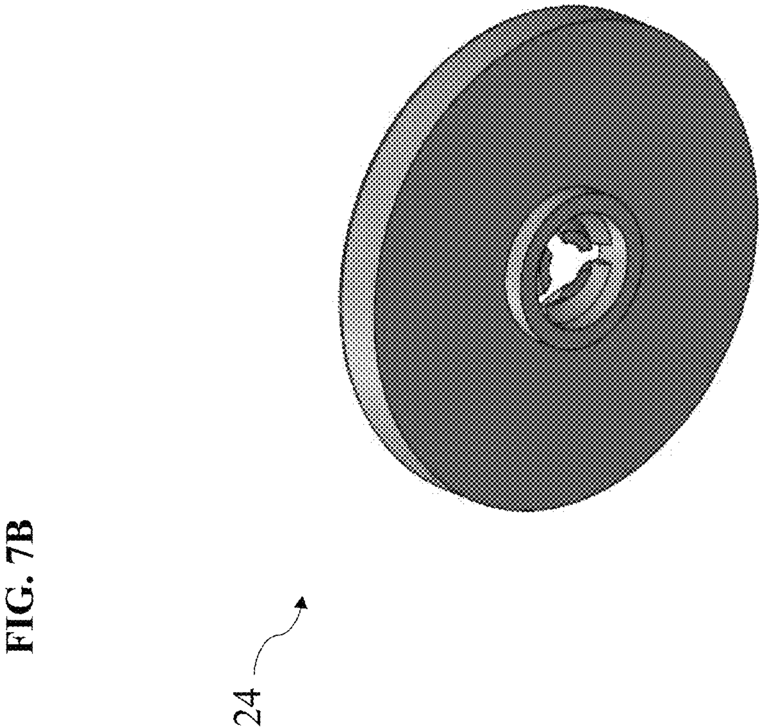
FIG. 7B is a perspective view of a plunger cap according to the embodiment in FIG. 7A.
Figure 7A:
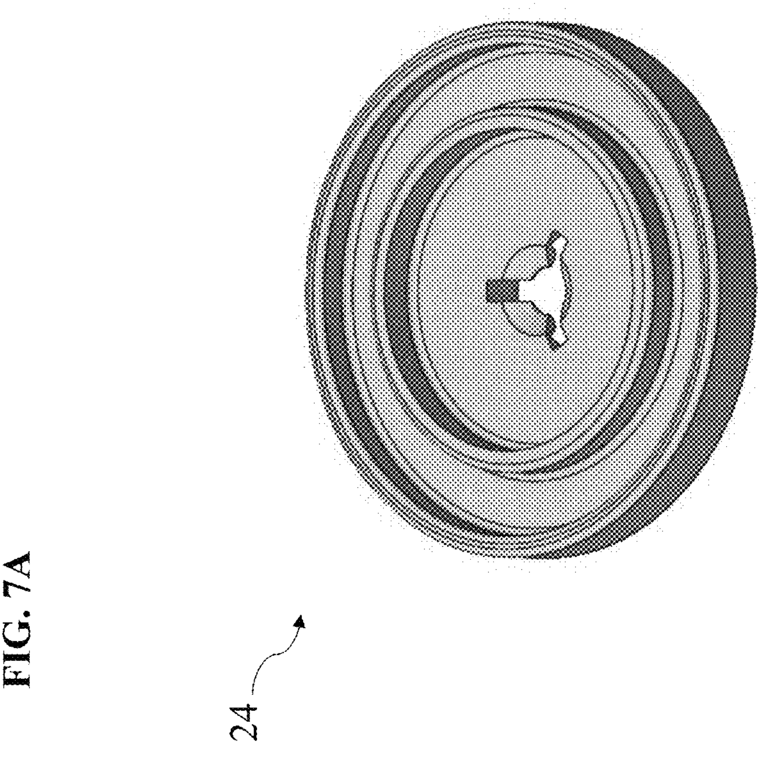
FIG. 7A is a perspective view of a plunger cap according to one or more embodiments herein.
Figure 8B:
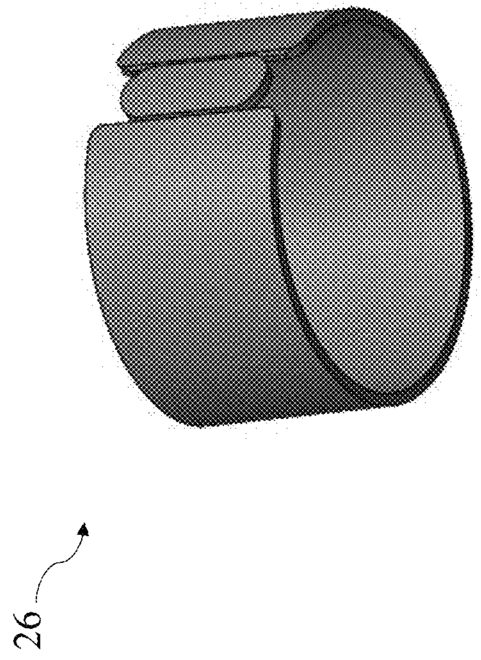
FIG. 8B is a perspective view of a locking mechanism according to one or more embodiments described in FIG. 8A.
Figure 8A:
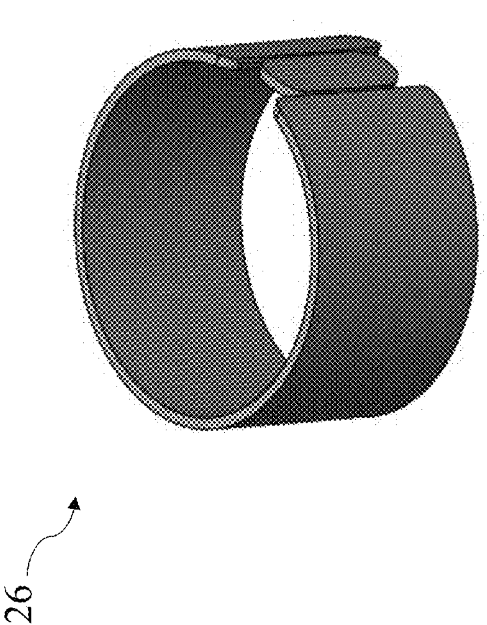
FIG. 8A is a perspective view of a locking mechanism according to one or more embodiments described herein.

Referring to FIGS. 1A-1B, the device 10 comprises a capsule body 12 having a cap portion 14 and an elongate portion 18 for storing chemical and/or biological material 20 therein (see also FIGS. 5A-5B). FIG. 1A illustrates a plunger 22 in a non-activated state such that the chemical and/or biological material 20 have not been released (see also FIGS. 2 and 3A-3B). The plunger 22 is positioned within the elongate portion 18 and further comprises a plunger cap 24 and locking mechanism 26 (see also FIGS. 7A-7B and 8A-8B). The plunger cap 24 fits on an end of the plunger 22 opposing a cutting mechanism 28 (see also FIGS. 6A-6B). The locking mechanism 26 is a ring configured to wrap around an end of the plunger 22 adjacent the plunger cap 24. The locking mechanism 26 is removed before plunger 22 activation (see FIGS. 1B and 4A-4B). The locking mechanism 26 prevents activation of the plunger 22 before a selected time by preventing the plunger 22 and/or plunger cap 24 from being pushed and/or depressed.

FIG. 1B illustrates the plunger 22 in an activated state such that the chemical and/or biological material 20 is released into the container 16. Referring to FIG. 1B, the device 10 comprises a capsule body 12 having a cap portion 14 and an elongate portion 18. The plunger 22 is in an activated and/or depressed state such that material 20 hosted within the capsule body 12 is released. The locking mechanism 26 is removed, allowing the plunger 22 to be activated. Specifically, the plunger 22 and plunger cap 24 have been pushed toward the capsule body 12 to release the chemical and/or biological material 20 into the container 16. In the activated state, the plunger cap 24 is in contact or adjacent to the capsule body 12 and/or the elongate portion 18 of the capsule body 12.

FIG. 2 illustrates a cross-section of a capsule 10 according to one or more embodiments herein comprising chemical and/or biological material 20 therein. The device 10 comprises a capsule body 12 having a cap portion 14 and elongate portion 18. FIG. 2 further illustrates a frangible bottom 30 on an end of the elongate portion 18 configured for suspension within a container 16 (see also FIG. 3B). The plunger 22 is in a non-activated state such that the frangible bottom 30 is intact and the chemical and/or biological material 20 is stored within the capsule body 12 and plunger 22. Furthermore, the device 10 comprises a plunger cap 24 and locking mechanism 26 wherein the locking mechanism 26 prevents premature activation of the plunger 22.

Figures 3A, 3B:
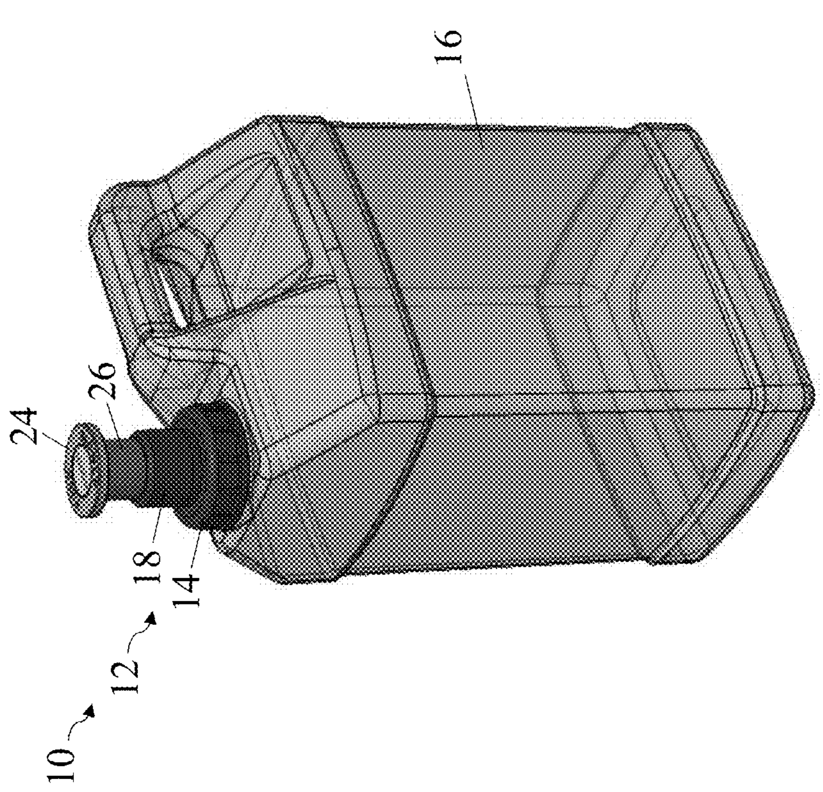
FIG. 3A is a perspective view of a capsule installed on a container according to one or more embodiments herein.
FIG. 3B is a perspective view of a capsule installed on a container according to the embodiment in FIG. 3A.

In one or more embodiments as illustrated in FIGS. 3-4, a device 10 comprises a capsule body 12 having a cap portion 14 configured for threadably securing to a mouth or opening of a container 16. In addition, the capsule body 12 comprises an elongate portion 18 for hosting a plunger 22 and chemical and/or biological material 20 therein, and a frangible bottom 30. The frangible bottom 30 separates chemical and/or biological material 20 from contents within the container 16. The plunger 22 comprises a cutting mechanism 28 configured for disrupting or breaking the frangible bottom 30 when the plunger 22 is activated. FIGS. 3A-3B illustrate a device 10 in a non-activated state such that chemical and/or biological material 20 is maintained in the device 10 and the frangible bottom 30 is intact. FIGS. 4A-4B illustrate a device 10 in an activated state such that the chemical and/or biological material 20 is released into the container 16 and the frangible bottom 30 is disrupted.

Although the present disclosure has been described with reference to preferred embodiments, workers skilled in the art will recognize that changes may be made in form and detail without departing from the spirit and scope of the disclosure.

What is claimed is:

1. A device for delivering biological material to a medium comprising:

a capsule comprising a cap portion configured to removably secure the capsule to a mouth of a container and an elongate portion comprising a cavity defined at least in part by a frangible bottom, wherein the cavity comprises biological material therein; and a plunger comprising:

a first end and a second end;

one or more walls defining an internal volume of the plunger, the one or more walls moveable along an inner surface of the capsule when the plunger is depressed; and a shaft disposed at least partially within the internal volume and connected to the second end of the plunger, the shaft including a disrupting mechanism at the first end of the plunger and the disrupting mechanism positioned external to the internal volume of the plunger, wherein the disrupting mechanism is configured to break the frangible bottom when the plunger is depressed;

wherein the first end of the plunger extends within the cavity of the capsule, and wherein the second end of the plunger extends outward from the cavity and the elongate portion of the capsule.

2. The device of claim 1, wherein the one or more walls defining the internal volume of the plunger are moveable in an axial direction relative to the capsule when the plunger is depressed.

3. The device of claim 1, wherein the biological material is retained within the internal volume of the plunger between the one or more walls and the frangible bottom of the capsule, and wherein the biological material is forced out of the cavity of the capsule by the plunger when the plunger is depressed.

4. The device of claim 1, wherein the one or more walls of the plunger comprise a shoulder portion configured to retain at least the first end of the plunger within the cavity of the capsule when the plunger is in a non-activated state.

5. The device of claim 4, wherein the elongate portion of the capsule comprises a shoulder portion configured to interfere with the shoulder portion of the plunger to retain the plunger at least partially within the capsule.

6. The device of claim 1 further comprising a locking mechanism configured to prevent the plunger from being depressed, wherein the locking mechanism is slidable on the plunger.

7. The device of claim 6, wherein the device further comprises a plunger cap connected to the second end of the plunger; and wherein the locking mechanism engages the plunger, the plunger cap maintaining the locking mechanism in position between the plunger cap and the elongate portion of the capsule until manual removal of the locking mechanism by a user.

8. The device of claim 7, wherein the locking mechanism comprises a ring portion and a tearable portion, and wherein the locking mechanism is configured for manual removal by a user by separating the tearable portion from the ring portion and pulling the ring portion off of the plunger.

9. The device of claim 1 further comprising a sealing member disposed between the one or more walls of the plunger and the inner surface of the capsule.

10. A system for delivering biological material to a medium comprising:

a container comprising the medium;

a capsule comprising a cap portion configured to removably secure the capsule to a mouth of the container and an elongate portion comprising a cavity defined at least in part by a frangible bottom, wherein the cavity comprises biological material therein; and a plunger comprising:

a first end and a second end;

one or more walls defining an internal volume of the plunger, the one or more walls moveable along an inner surface of the capsule when the plunger is depressed; and a shaft disposed at least partially within the internal volume and connected to the second end of the plunger, the shaft including a disrupting mechanism at the first end of the plunger and the disrupting mechanism positioned external to the internal volume of the plunger, wherein the disrupting mechanism is configured to break the frangible bottom when the plunger is depressed;

wherein the first end of the plunger extends within the cavity of the capsule, and wherein the second end of the plunger extends outward from the cavity and the elongate portion of the capsule.

11. The system of claim 10, wherein the container is a plastic F-style container.

12. The system of claim 10, wherein a volume of the container is approximately 2.5 gallons.

13. The system of claim 10, wherein:

the one or more walls defining the internal volume of the plunger are moveable in an axial direction relative to the capsule when the plunger is depressed;

the biological material is retained within the internal volume of the plunger between the one or more walls and the frangible bottom of the capsule, and wherein the biological material is forced out of the cavity of the capsule by the plunger when the plunger is depressed; and the plunger further comprises a shoulder portion configured to retain at least the first end of the plunger within the cavity of the capsule when the plunger is in a non-activated state.

14. The system of claim 10 further comprising:

a locking mechanism configured to prevent the plunger from being depressed, wherein the locking mechanism comprises a ring portion and a tearable portion; and a plunger cap connected to the second end of the plunger; wherein the locking mechanism engages the plunger, the plunger cap maintaining the locking mechanism in position between the plunger cap and the elongate portion of the capsule until manual removal of the locking mechanism by a user separating the tearable portion from the ring portion and pulling the ring portion off of the plunger.

15. A method for delivering biological material to a medium comprising:

securing a capsule to a mouth of a container, the capsule comprising a cap portion configured to removably secure the capsule to a mouth of the container and an elongate portion comprising a cavity defined at least in part by a frangible bottom, wherein the cavity comprises biological material therein;

suspending the elongate portion of the capsule into a cavity of the container;

depressing a plunger, the plunger comprising:

a first end and a second end;

one or more walls defining an internal volume of the plunger, the one or more walls moveable along an inner surface of the capsule; and a shaft disposed at least partially within the internal volume and connected to the second end of the plunger, the shaft including a disrupting mechanism at the first end of the plunger and the disrupting mechanism positioned external to the internal volume of the plunger;

wherein the first end of the plunger extends within the cavity of the capsule, and wherein the second end of the plunger extends outward from the cavity and the elongate portion of the capsule;

disrupting the frangible bottom of the capsule; and releasing the biological material into the container.

16. The method of claim 15, wherein releasing the biological material into the container comprises forcing the biological material into the container using the plunger.

17. The method of claim 15 further comprising removing a locking mechanism from the plunger to allow depression of the plunger, wherein the locking mechanism is engaged with the plunger in position between the elongate portion of the capsule and a plunger cap connected to the second end of the plunger.

18. The method of claim 17, wherein removing the locking mechanism comprises:

separating a tearable portion from a ring portion of the locking mechanism; and pulling the ring portion of the locking mechanism off of the plunger.

19. The method of claim 15 further comprising shaking the container to combine the biological material with a liquid medium provided within the container.

20. The method of claim 15, wherein the biological material comprises a bio-fungicide, bio-herbicide, bio-fertilizer, and/or bio-insecticide/pesticide.

* * * * *